US010081749B2

(12) United States Patent
Taniguchi et al.

(10) Patent No.: US 10,081,749 B2
(45) Date of Patent: *Sep. 25, 2018

(54) COMPOSITION CONTAINING TRIFLUOROETHYLENE

(71) Applicant: Asahi Glass Company, Limited, Tokyo (JP)

(72) Inventors: Tomoaki Taniguchi, Tokyo (JP); Hidekazu Okamoto, Tokyo (JP); Shoji Furuta, Tokyo (JP); Yu Takeuchi, Tokyo (JP)

(73) Assignee: AGC Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/851,473

(22) Filed: Sep. 11, 2015

(65) Prior Publication Data

US 2016/0002518 A1 Jan. 7, 2016

Related U.S. Application Data

(63) Continuation of application No. PCT/JP2014/061764, filed on Apr. 25, 2014.

(30) Foreign Application Priority Data

Apr. 30, 2013 (JP) .................... 2013-095491

(51) Int. Cl.
| | |
|---|---|
| C09K 5/04 | (2006.01) |
| C09K 3/30 | (2006.01) |
| B01F 17/00 | (2006.01) |
| C09K 3/00 | (2006.01) |
| C07C 17/278 | (2006.01) |
| C07C 17/383 | (2006.01) |

(52) U.S. Cl.
CPC .......... C09K 5/044 (2013.01); B01F 17/0085 (2013.01); C07C 17/278 (2013.01); C07C 17/383 (2013.01); C09K 3/00 (2013.01); C09K 3/30 (2013.01); C09K 5/045 (2013.01); C09K 2205/112 (2013.01); C09K 2205/12 (2013.01); C09K 2205/126 (2013.01); C09K 2205/22 (2013.01)

(58) Field of Classification Search
CPC .......... C09K 5/044; C09K 5/045; C09K 3/30; C09K 3/00; C09K 2205/112; C09K 2205/12; C09K 2205/22; C09K 2205/126; C07C 17/383; C07C 17/278; C07C 21/18; B01F 17/0085
USPC .................. 252/67, 364; 516/12, 8
See application file for complete search history.

(56) References Cited

U.S. PATENT DOCUMENTS

| | | | | |
|---|---|---|---|---|
| 2,802,887 A | * | 8/1957 | Smith ............... | C07C 17/23 570/156 |
| 3,073,870 A | | 1/1963 | Marquis | |
| 3,564,064 A | * | 2/1971 | Nakagawa ......... | C07C 17/23 570/156 |
| 5,059,729 A | * | 10/1991 | Gervasutti .......... | C07C 17/00 570/175 |
| 5,387,729 A | | 2/1995 | Lerot et al. | |
| 6,068,756 A | * | 5/2000 | Gimenez ............ | C25B 3/04 205/459 |
| 7,708,903 B2 | | 5/2010 | Sievert et al. | |
| 8,071,826 B2 | * | 12/2011 | Van Der Puy ..... | C07C 17/206 570/159 |
| 9,353,303 B2 | * | 5/2016 | Fukushima ........ | F25B 9/002 |
| 9,902,672 B2 | * | 2/2018 | Wang ................. | C07C 17/23 |
| 2006/0217577 A1 | * | 9/2006 | Mukhopadhyay .. | C07C 17/23 570/156 |
| 2007/0191652 A1 | | 8/2007 | Ohno et al. | |
| 2010/0090156 A1 | | 4/2010 | Nappa et al. | |
| 2010/0191024 A1 | | 7/2010 | Uenveren et al. | |
| 2015/0376486 A1 | * | 12/2015 | Hashimoto ........ | C09K 5/045 252/67 |
| 2016/0075927 A1 | | 3/2016 | Fukushima | |
| 2016/0332937 A1 | * | 11/2016 | Nakamura .......... | C07C 17/25 |
| 2016/0332938 A1 | * | 11/2016 | Nakamura .......... | C07C 17/25 |
| 2016/0333243 A1 | * | 11/2016 | Fukushima ........ | C09K 5/045 |
| 2016/0340565 A1 | * | 11/2016 | Tasaka .............. | C09K 5/045 |
| 2016/0347693 A1 | * | 12/2016 | Fukushima ........ | C07C 17/23 |
| 2017/0008823 A1 | * | 1/2017 | Nakamura .......... | C07C 17/25 |

FOREIGN PATENT DOCUMENTS

| | | |
|---|---|---|
| CN | 101947445 A | 1/2011 |
| EP | 0 496 446 A1 | 7/1992 |
| JP | 2-178238 A | 7/1990 |
| JP | 2005-314376 | 11/2005 |

(Continued)

OTHER PUBLICATIONS

Bao-Chuan Meng et al., "Selective Liquid-phase Hydrodechlorination of Chlorotrifluoroethylene over Palladium-Supported Catalysts : Activity and Deactivation", Catal Lett (2010), 138:68-75. (Year: 2010).*
International Search Report dated Aug. 5, 2014 in PCT/JP2014/061764 filed Apr. 25, 2014.
Extended European Search Report dated Nov. 25, 2016 in Patent Application No. 14791990.6.
U.S. Appl. No. 14/946,037, filed Nov. 19, 2015, Masato Fukushima.
U.S. Appl. No. 15/229,724, filed Aug. 5, 2016, Mai Tasaka, et al.
U.S. Appl. No. 14/850,035, filed Sep. 10, 2015, Mai Hashimoto, et al.

*Primary Examiner* — Douglas J McGinty
(74) *Attorney, Agent, or Firm* — Oblon, McClelland, Maier & Neustadt, L.L.P.

(57) ABSTRACT

A composition is provided containing HFO-1123 having a low GWP, which is useful as a heat transfer composition, an aerosol sprayer, a foaming agent, a blowing agent, a solvent or the like. A composition containing HFO-1123, and at least one first compound selected from the group consisting of HFO-1132, HFO-1132a, CFO-1113, HCFO-1122, HCFO-1122a, HFC-143 and methane.

10 Claims, No Drawings

(56) References Cited

FOREIGN PATENT DOCUMENTS

| | | | |
|---|---|---|---|
| JP | 2010-533151 | 10/2010 | |
| WO | WO 2012000853 A1 * | 1/2012 | ............. B01J 21/18 |
| WO | WO 2012/157762 | 11/2012 | |
| WO | WO 2012/157764 | 11/2012 | |
| WO | WO-2012157764 A1 * | 11/2012 | ............. F25B 9/002 |

* cited by examiner

COMPOSITION CONTAINING TRIFLUOROETHYLENE

TECHNICAL FIELD

The present invention relates to a composition containing trifluoroethylene, particularly a composition useful as a heat transfer composition.

BACKGROUND ART

A new refrigerant to be used for refrigerating, air-conditioning and heat pump apparatus is required due to new environmental regulations, and compounds having a low global warming potential (GWP) have attracted attention.

In recent years, as a compound having a low global warming potential, trifluoroethylene (HFO-1123) attracts attention. In this specification, abbreviated names of halogenated hydrocarbon compounds are described in brackets after the compound names, and in this specification, the abbreviated names are employed instead of the compound names as the case requires.

HFO-1123 has been used for a refrigerating and heat transfer fluid, an aerosol spray, a foaming/expanding agent and the like, and in recent years, it is expected to be promising as an alternative to a saturated HFC (hydrofluorocarbon) type refrigerant having a high GWP.

For example, Patent Document 1 discloses a composition containing HFO-1123 as a working medium to be used for a heat cycle system.

However, a composition containing HFO-1123, which can be used for various applications, has been desired.

PRIOR ART DOCUMENT

Patent Document

Patent Document 1: WO2012/157764

DISCLOSURE OF INVENTION

Technical Problem

The object of the present invention is to provide a composition containing HFO-1123 having a low GWP and useful as a heat transfer composition, an aerosol spray, a foaming agent, a blowing agent, a solvent and the like.

Solution to Problem

The present inventors have found that a composition obtainable in preparation of HFO-1123 contains a small amount of a specific compound other than HFO-1123 and accomplished the present invention.

The present invention provides a composition containing trifluoroethylene (HFO-1123) and at least one first compound selected from the group consisting of E-1,2-difluoroethylene (HFO-1132), Z-1,2-difluoroethylene (HFO-1132), 1,1-difluoroethylene (HFO-1132a, VdF), chlorotrifluoroethylene (CFO-1113, CTFE), 1-chloro-2,2-difluoroethylene (HCFO-1122), E-1-chloro-1,2-difluoroethylene (HCFO-1122a), Z-1-chloro-1,2-difluoroethylene (HCFO-1122a), 1,1,2-trifluoroethane (HFC-143) and methane.

The present invention further provides a method for producing a composition containing trifluoroethylene by gas-phase hydrogen reduction of chlorotrifluoroethylene, wherein chlorotrifluoroethylene and hydrogen are reacted in the presence of a palladium catalyst at 80° C. or higher, and the obtained reaction product is distilled to obtain trifluoroethylene containing at least one compound selected from the group consisting of E-1,2-difluoroethylene, Z-1,2-difluoroethylene, chlorotrifluoroethylene, 1-chloro-2,2-difluoroethylene and 1,1-difluoroethylene.

The present invention further provides a method for producing a composition containing trifluoroethylene by a synthetic reaction involving heat decomposition in the presence of a heating medium from a mixture of chlorodifluoromethane and chlorofluoromethane, wherein the reaction is carried out at from 400 to 1,200° C., and the obtained reaction product is distilled to obtain trifluoroethylene containing at least one compound selected from the group consisting of E-1,2-difluoroethylene, Z-1,2-difluoroethylene, 1,1-difluoroethylene, chlorotrifluoroethylene, tetrafluoroethylene, fluoroethylene, 1,1,1-trifluoroethane, difluoromethane, trifluoromethane and pentafluoroethane.

Advantageous Effects on Invention

According to the present invention, a composition containing HFO-1123 which is expected as a new refrigerant having a low GWP as an alternative to greenhouse gases 1,1,1,2-tetrafluoroethane (HFC-134a) and R410A (a mixed medium of difluoromethane (HFC-32) and pentafluoroethane (HFC-125) in a mass ratio of 1:1), useful for various applications, can be obtained.

DESCRIPTION OF EMBODIMENTS

The composition according to a first embodiment of the present invention contains HFO-1123 and a first compound. The first compound is at least one compound selected from the group consisting of HFO-1132, VdF, CTFE, HCFO-1122, HCFO-1122a, HFC-143 and methane. In this composition, the proportion of each compound contained is preferably less than 0.5 mass % based on the total amount of HFO-1123 and the first compound(s). Further, the total proportion of the first compound(s) contained in the composition is preferably less than 0.5 mass % based on the total amount of HFO-1123 and the first compound(s). Further, the lower limit of the total proportion of the first compound(s) is preferably 0.0001 mass %.

As described hereinafter, production of HFO-1123 may be carried out, for example, by (I) a method of subjecting chlorotrifluoroethylene (CTFE) (CFO-1113) to hydrogen reduction in a gas phase. Accordingly, in a certain embodiment, a compound other than HFO-1123 obtainable by a method of subjecting CTFE to hydrogen reduction in a gas phase is present in the formed composition obtainable together with HFO-1123. Further, in a certain embodiment, impurities present in CTFE as a material for production of HFO-1123 are present as they are during the reaction of forming HFO-1123, and are present in the formed composition obtainable together with HFO-1123.

That is, the composition according to a second embodiment of the present invention contains HFO-1123 and the above first compound and further contains at least one second compound selected from the group consisting of 1,1-difluoroethane (HFC-152a), 2-chloro-1,1-difluoroethane (HCFC-142), 1-chloro-1,1-difluoroethane (HCFC-142b), 1-chloro-1,2,2-trifluoroethane (HCFC-133), 1-chloro-1,1,2-trifluoroethane (HCFC-133b), 1,2-dichloro-1,1,2-trifluoroethane (HCFC-123a), 1,1,2-trichloro-1,2,2-trifluoroethane (CFC-113) and E- and/or Z-1,2-dichloro-1,2-difluoroethylene (CFO-1112). In this composition, the proportion of each second compound contained is preferably less than 0.5 mass % based on the total amount of HFO-1123, the first compound(s) and the second compound(s). Further, the total proportion of the second compound(s) contained in the composition is preferably less than 0.5 mass % based on the total amount of HFO-1123, the first compound(s) and the second compound(s). Further, the lower limit of the total proportion of the second compound(s) is preferably 0.0001 mass %.

Further, as described hereinafter, HFO-1123 may be produced by (II) a synthetic reaction involving thermal decomposition of a mixture of chlorodifluoromethane (HCFC-22 (hereinafter referred to as R22)) and chlorofluoromethane (HCFC-31 (hereinafter referred to as R31)) in the presence of a heating medium. Accordingly, in a certain embodiment, a compound other than HFO-1123 obtainable by synthesis involving heat decomposition of a mixture of R22 and R31 is present in the formed composition obtainable together with HFO-1123. Further, in a certain embodiment, impurities present in R22 or R31 as a material for production of HFO-1123 are present as they are during the reaction for forming HFO-1123 and are present in the formed composition obtainable together with HFO-1123.

That is, the composition according to a third embodiment of the present invention contains HFO-1123 and the above first compound and further contains at least one third compound selected from the group consisting of tetrafluoroethylene (FO-1114, TFE), E- and/or Z-1-chloro-2-fluoroethylene (HCFO-1131), fluoroethylene (HFO-1141), 3,3-difluoropropene (HFO-1252zf), 3,3,3-trifluoropropene (HFO-1243zf), 2,3,3,3-tetrafluoropropene (HFO-1234yf), E- and/or Z-1,3,3,3-tetrafluoropropene (HFO-1234ze), hexafluoropropene (FO-1216, HFP), pentafluoroethane (HFC-125), 1,1,2,2-tetrafluoroethane (HFC-134), 1,1,1,2-tetrafluoroethane (HFC-134a), 1,1,1-trifluoroethane (HFC-143a), 1-chloro-1,2,2,2-tetrafluoroethane (HCFC-124), 1-chloro-1,1,2,2-tetrafluoroethane (HCFC-124a), 1,1,1,2,2,3,3-heptafluoropropane (HFC-227ca), 1,1,1,2,3,3,3-heptafluoropropane (HFC-227ea), 1,1,1,3,3,3-hexafluoropropane (HFC-236fa), 1,1,1,2,3,3-hexafluoropropane (HFC-236ea), dichlorodifluoromethane (CFC-12), chlorodifluoromethane (HCFC-22), chlorofluoromethane (HCFC-31), difluoromethane (HFC-32), trifluoromethane (HFC-23), fluoromethane (HFC-41), chloromethane and perfluorocyclobutane (RC-318). In this composition, the proportion of each third compound contained is preferably less than 0.5 mass % based on the total amount of HFO-1123, the first compound(s) and the third compound(s). Further, the total proportion of the third compound(s) contained in the composition is preferably less than 0.5 mass % based on the total amount of HFO-1123, the first compound(s) and the third compound(s). The lower limit of the total proportion of the third compound(s) is preferably 0.0001 mass %.

In this specification, abbreviated names of halogenated hydrocarbon compounds contained in the composition of the present invention are described, and chemical formulae and names of the compounds represented by the abbreviated names are as identified in Tables 1 and 2.

TABLE 1

| Abbreviated names | Chemical formulae | Compound names |
|---|---|---|
| | $CH_4$ | Methane |
| | $CH_3Cl$ | Chloromethane |
| CFC-12 | $CF_2Cl_2$ | Dichlorodifluoromethane |
| HCFC-22 | $CHF_2Cl$ | Chlorodifluoromethane |
| HFC-23 | $CHF_3$ | Trifluoromethane |
| HFC-32 | $CH_2F_2$ | Difluoromethane |
| HCFC-31 | $CH_2FCl$ | Chlorofluoromethane |
| HFC-41 | $CH_3F$ | Fluoromethane |
| CFC-113 | $CCl_2FCF_2Cl$ | 1,1,2-Trichloro-1,2,2-trifluoroethane |
| HCFC-123a | $CF_2ClCHFCl$ | 1,2-Dichloro-1,1,2-trifluoroethane |
| HCFC-124 | $CHFClCF_3$ | 1-Chloro-1,2,2,2-tetrafluoroethane |
| HCFC-124a | $CF_2ClCHF_2$ | 1-Chloro-1,1,2,2-tetrafluoroethane |
| HFC-125 | $CHF_2CF_3$ | Pentafluoroethane |
| HCFC-133 | $CHFClCHF_2$ | 1-Chloro-1,2,2-trifluoroethane |
| HCFC-133b | $CF_2ClCH_2F$ | 1-Chloro-1,1,2-trifluoroethane |
| HFC-134 | $CHF_2CHF_2$ | 1,1,2,2-Tetrafluoroethane |
| HFC-134a | $CF_3CH_2F$ | 1,1,1,2-Tetrafluoroethane |
| HCFC-142 | $CH_2ClCHF_2$ | 2-Chloro-1,1-difluoroethane |
| HCFC-142b | $CF_2ClCH_3$ | 1-Chloro-1,1-difluoroethane |
| HFC-143 | $CHF_2CH_2F$ | 1,1,2-Trifluoroethane |
| HFC-143a | $CF_3CH_3$ | 1,1,1-Trifluoroethane |
| HFC-152a | $CHF_2CH_3$ | 1,1-Difluoroethane |
| HFC-227ca | $CF_3CF_2CHF_2$ | 1,1,1,2,2,3,3-Heptafluoropropane |
| HFC-227ea | $CF_3CHFCF_3$ | 1,1,1,2,3,3,3-Heptafluoropropane |
| HFC-236fa | $CF_3CH_2CF_3$ | 1,1,1,3,3,3-Hexafluoropropane |
| HFC-236ea | $CF_3CHFCHF_2$ | 1,1,1,2,3,3-Hexafluoropropane |

TABLE 2

| Abbreviated names | Chemical formulae | Compound names |
|---|---|---|
| CFO-1112 | $CFCl\!=\!CFCl$ | E- and/or Z-1,2-Dichloro-1,2-difluoroethylene |
| CFO-1113 | $CF_2\!=\!CFCl$ | Chlorotrifluoroethylene |
| FO-1114 | $CF_2\!=\!CF_2$ | Tetrafluoroethylene |
| HCFO-1122 | $CF_2\!=\!CHCl$ | 1-Chloro-2,2-difluoroethylene |
| HCFO-1122a | $CFCl\!=\!CHF$ | E- and/or Z-1-Chloro-1,2-difluoroethylene |
| HFO-1123 | $CF_2\!=\!CHF$ | Trifluoroethylene |
| HCFO-1131 | $CHF\!=\!CHCl$ | E- and/or Z-1-Chloro-2-fluoroethylene |
| HFO-1132 | $CHF\!=\!CHF$ | E- and/or Z-1,2-Difluoroethylene |
| HFO-1132a | $CF_2\!=\!CH_2$ | 1,1-Difluoroethylene |
| HFO-1141 | $CHF\!=\!CH_2$ | Fluoroethylene |
| FO-1216 | $CF_3CF\!=\!CF_2$ | Hexafluoropropene |
| HFO-1234yf | $CF_3CF\!=\!CH_2$ | 2,3,3,3-Tetrafluoropropene |
| HFO-1234ze | $CF_3CH\!=\!CHF$ | E- and/or Z-1,3,3,3-Tetrafluoropropene |
| HFO-1243zf | $CF_3CH\!=\!CH_2$ | 3,3,3-Trifluoropropene |
| HFO-1252zf | $CHF_2CH\!=\!CH_2$ | 3,3-Difluoropropene |
| RC-318 | $-\!(CF_2CF_2CF_2CF_2)\!-$ | Perfluorocyclobutane |

The compositions of the present invention are useful as a heat transfer composition, an aerosol spray, a foaming agent, a blowing agent, a solvent, a cleaning agent, a carrier fluid, a displacement drying agent, a buffing compound, a polymerization medium, an expanding agent for polyolefin and polyurethane, a gaseous dielectric, a fire-extinguishing agent or a liquid or gaseous fire-extinguishing agent. Particularly the composition having a total proportion of the first compound(s) of less than 0.5 mass % in the first embodiment has a low GWP and is useful as a new refrigerant which replaces greenhouse gases.

Further, the composition having a total proportion of the first compound(s) of less than 0.5 mass % and having a total proportion of the second compound(s) of less than 0.5 mass % in the second embodiment has a low GWP and is useful as a new refrigerant which replaces greenhouse gases. In the second embodiment, the total amount of the first compound(s) and the second compound(s) is more preferably less than 0.5 mass %.

Further, the composition having a total proportion of the first compound(s) of less than 0.5 mass % and having a total proportion of the third compound(s) of less than 0.5 mass % in the third embodiment has a low GWP and is useful. In the third embodiment, the total amount of the first compound(s) and the third compound(s) is more preferably less than 0.5 mass %.

Here, such a proportion is a proportion based on the total amount with trifluoroethylene in the same manner as above.

Further, the composition according to an embodiment of the present invention may function as a working fluid which transfers heat from a heat source to a heatsink. Particularly as the heat transfer composition, it is useful as a refrigerant in a cycle in which the fluid undergoes phase change from a gas to a liquid and from a liquid to a gas. A heat transfer system may, for example, be an air-conditioner, a freezer, a refrigerator, a heat pump, a water chiller, a flooded evaporative cooler, a direct expansion cooler, a walk-in cooler, a movable refrigerator, a movable air-conditioning unit or a combination thereof.

Here, a movable refrigerating apparatus, a movable air-conditioner or a movable heating apparatus means an optional refrigerating, air-conditioning or heating apparatus to be incorporated in a road, rail, ocean or air transport unit. Further, a movable refrigerating or air-conditioning unit contains an apparatus known as "intermodal" system independent of an optional transfer carrier. Such an "intermodal system" may be "a container (a combined ocean/land transportation)" and "a swap body (a combined road/rail transportation)".

Further, a fixed heat transfer system is a system associated with or fixed in various buildings. Such a fixed system may be a fixed air-conditioner or a heat pump (such as a cooler, a high temperature heat pump, a housing, commercial or industrial air-conditioning system, and an exterior connected to a building, such as a window, a ductless, duct or packaged terminal air-conditioner, a cooler or a rooftop system, although the system is not limited thereto). In the fixed refrigerating apparatus, the composition of the present invention is useful for equipment such as a commercial, industrial or housing refrigerator or freezer, an ice-making machine, a built-in cooler or freezer, a flooded evaporative cooler, a direct expansion cooler, a walk-in or reach-in cooler or freezer, or a combination thereof. The composition according to an embodiment of the present invention may be used, for example, for a refrigerating system in a supermarket.

<Production of HFO-1123>

As an embodiment of production of HFO-1123, two embodiments of (I) hydrogen reduction of CTFE and (II) synthesis involving heat decomposition of R22 and R31 may be mentioned.

Now, these embodiments and compounds obtained together with HFO-1123 will be described.

(I) Hydrogen Reduction of CTFE

A material compound CTFE (CFO-1113) and hydrogen are reacted in a gas phase in a reactor having a catalyst layer filled with a catalyst-supporting carrier to form a gas containing HFO-1123.

The main reaction in the reactor in this embodiment is shown in the following formula (1):

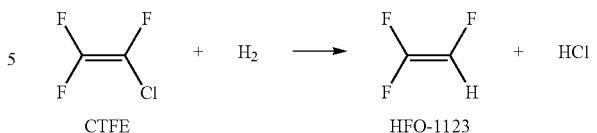

(1)

<Material Composition>

The material composition to be used for formation of HFO-1123 by hydrogen reduction of CTFE contains CTFE and hydrogen.

With respect to the ratio of CTFE and hydrogen in the material composition, the proportion of hydrogen is within a range of from 0.01 to 4.0 mole per 1 mole of CTFE. That is, the molar ratio of hydrogen supplied to CTFE supplied into the reactor (hydrogen/CTFE where CTFE is the molar amount of CTFE supplied and hydrogen is the molar amount of hydrogen supplied) is from 0.01 to 4.0.

When the hydrogen/CTFE ratio is within the above range, the inversion rate of the material component particularly the inversion rate of CTFE can be made high. Further, the proportion of components other than HFO-1123 i.e. by-products in the obtained reaction product can be suppressed. The hydrogen/CTFE ratio is more preferably from 0.1 to 4.0, particularly preferably from 0.1 to 2.

The inversion rate is also called a reaction rate, and means the proportion (mol %) of the material component reacted. For example, when the proportion (yield) of the material component in an outlet gas is X %, the inversion rate is (100−X) %.

<Reactor>

As the reactor, a known reactor in which a catalyst layer filled with a catalyst-supporting carrier can be formed, may be mentioned. As a material of the reactor, glass, iron, nickel or an alloy containing iron or nickel as the main component may, for example, be mentioned. The pressure in the reactor is preferably ordinary pressure in view of handling efficiency.

<Catalyst and Catalyst-Supporting Carrier>

The catalyst is preferably a palladium catalyst. The palladium catalyst is preferably used as supported on a carrier. The palladium catalyst may be palladium single substance or may be a palladium alloy. Further, the palladium catalyst may be a catalyst having a mixture of palladium with another metal supported or may be a composite catalyst having palladium and another metal separately supported. As a palladium alloy catalyst, a palladium/platinum alloy catalyst or a palladium/rhodium alloy catalyst may, for example, be mentioned.

The catalyst is preferably a catalyst having only palladium or a palladium alloy supported on a carrier, or a catalyst having a mixture of palladium with a metal other than palladium supported on a carrier. A catalyst having palladium and a metal other than palladium supported on a carrier tends to have high catalyst durability as compared with a catalyst having only palladium supported on a carrier.

The metal other than palladium may, for example, be a group 8 element (such as iron, ruthenium or osmium), a group 9 element (such as cobalt, rhodium or iridium), a group 10 element (such as nickel or platinum) or gold. Such other metals may be used alone or in combination of two or more. The proportion of such other metal is preferably from 0.01 to 50 parts by mass per 100 parts by mass of palladium.

The carrier may, for example, be activated carbon or a metal oxide (such as alumina, zirconia or silica), and is preferably activated carbon in view of the activity, the durability and the reaction selectivity. The activated carbon may be one obtained from e.g. a plant material (such as wood, charcoal, fruit shell or coconut shell) or a mineral material (such as peat, lignite or coal), and is preferably one obtained from the plant material in view of the catalyst durability, particularly preferably coconut shell activated carbon. As the shape of activated carbon, formed coal having a length at a level of from 2 to 10 m, crushed coal of from about 4 to about 50 mesh, granular coal or the like may be mentioned, and in view of the activity, crushed coal of from 4 to 20 mesh or formed carbon having a length of from 2 to 5 mm is preferred.

The amount of palladium supported is preferably from 0.1 to 10 parts by mass, more preferably from 0.5 to 1 part by mass per 100 parts by mass of the activated carbon. When the amount of palladium supported is at least 0.1 part by mass, the reactivity of CTFE as the material compound and hydrogen will improve. When the amount of palladium supported is at most 10 parts by mass, an excessive temperature increase of the catalyst layer by the heat of reaction tends to be suppressed, and formation of by-products tends to be reduced. With respect to a carrier other than the activated carbon, the amount of palladium supported is preferably the same amount as in the case of the activated carbon.

<Catalyst Layer>

A catalyst layer is formed in the reactor by filling the reactor with the catalyst-supporting carrier. The density of the catalyst-supporting carrier in the catalyst layer is preferably from 0.5 to 1 g/cm$^3$, more preferably from 0.6 to 0.8 g/cm$^3$. When the density of the catalyst-supporting carrier is at least 0.5 g/cm$^3$, the amount of the catalyst-supporting carrier per unit volume tends to be large, and the amount of gas to be reacted tends to be large, whereby the productivity will improve. When the density of the catalyst-supporting carrier is at most 1 g/cm$^3$, an excessive temperature increase of the catalyst layer by the heat of reaction tends to be suppressed, and formation of by-products tends to be reduced. The portion filled with the catalyst-supporting carrier may be one or two in the reactor.

In order to carry out a gas-phase reaction, the temperature of the catalyst layer is a temperature of at least the dew point of the material composition (gas mixture) containing CTFE and hydrogen. The temperature of the catalyst layer is more preferably at least 80° C. in view of the reactivity, more preferably at least 180° C. with a view to improving the reactivity, further preferably within a range of from 220 to 240° C.

The temperature of the catalyst layer gradually decreases along with deterioration of the catalyst, and thus the reaction rate decreases. Accordingly, in order to maintain a high reaction rate, it is preferred to carry out operation to maintain the temperature of the catalyst layer to be sufficiently high. For example, in a case where the temperature is maintained by heating the catalyst layer from outside e.g. with a heating medium, the temperature of the heating medium may be gradually increased to increase the temperature of the catalyst layer.

Here, the temperature of the catalyst layer means the temperature of the catalyst layer maintained by heating from the outside. Usually, the material gas mixture is reacted in a part of the catalyst layer, and by the heat of reaction, the temperature at the reaction region (a region where the material gas mixture is reacted) is higher than the other catalyst layer region. The catalyst activity of the reaction region decreases with time, and usually the reaction region gradually moves from an inlet of the material gas mixture toward the downstream side in the gas flow direction. Further, in the downstream side of the reaction region, a high temperature gas formed in the reaction region flows, and the temperature of the downstream side is usually higher than the temperature of the catalyst layer, and the temperature gradually decreases with distance from the reaction region. Accordingly, the temperature of the catalyst layer means the temperature at the upstream side in the reaction region, that is, the temperature of the catalyst layer heated from the outside with e.g. a heating medium and having its temperature maintained.

Further, as mentioned above, the temperature at the reaction region where the material gas mixture is reacted and the region on the downstream side is higher than the temperature of the catalyst layer in the other region due to the heat of reaction. In the initial stage of operation of the reactor, the catalyst in the vicinity of the inlet of the gas contributes to the reaction, and as the catalyst deteriorates during operation of the reactor, the catalyst on the gas outlet side contributes to the reaction. In such a manner, during operation of the reactor, the reaction region in the catalyst layer gradually moves from the gas inlet side toward the gas outlet side. That is, since the portion at which the catalyst layer reaches the maximum temperature moves as the reaction region moves, it is preferred to dispose the measurement portion of a bulk thermometer on the gas inlet side of the catalyst layer in the initial stage of operation and to move the measurement portion toward the gas outlet side as the reaction proceeds to measure the maximum temperature of the catalyst layer.

The time of contact of CTFE as the material compound and the catalyst is preferably from 4 to 60 seconds, more preferably from 8 to 40 seconds. This contact time is calculated from the amount of the gas to be introduced to the reactor and the volume of the catalyst layer.

The linear velocity u of the material compound (gas) in the catalyst layer represented by the following formula is preferably from 0.1 to 100 cm/sec, more preferably from 1 to 30 cm/sec. This linear velocity u is a linear velocity of the material compound calculated from the amount of the gas to be introduced to the reactor and the volume of the catalyst layer. When the linear velocity u of the material compound is at least 0.1 cm/sec, the productivity will improve. When the linear velocity u of the material compound is at most 100 cm/sec, the reaction rate of the material compound and hydrogen will improve.

$$u=(W/100) \times V/S$$

In the formula, W is the concentration (mol %) of the material compound gas in the entire gas flowing through the catalyst layer, V is the flow rate (cm$^3$/sec) of the entire gas flowing through the catalyst layer, and S is the cross section (cm$^2$) of the catalyst layer perpendicular to the gas flow direction.

<Outlet Gas Component>

In such hydrogen reduction of CTFE, a composition containing HFO-1123 can be obtained as an outlet gas of the reactor. Compounds other than HFO-1123 contained in the outlet gas may, for example, be CTFE (CFO-1113) as the unreacted material, and HFO-1132, HFO-1132a, HCFO-1122, HCFO-1122a, HFC-143, methane, HFC-152a, HCFC-142, HCFC-142b, HCFC-133, HCFC-133b, HCFC-123a, CFC-113 and CFO-1112.

The above components other than HFO-1123 contained in the outlet gas may be removed by a known means such as distillation to the desired level. Particularly purification by distillation is preferred. And, CTFE separated may be recycled as a part of the material.

The composition containing HFO-1123 obtained by purification is preferably a composition containing, in addition to HFO-1123, at least one compound selected from the group consisting of E-1,2-difluoroethylene, Z-1,2-difluoroethylene, chlorotrifluoroethylene, 1-chloro-2,2-difluoroethylene and 1,1-difluoroethylene.

The proportion of each of the above compounds other than HFO-1123 contained is preferably less than 0.5 mass % based on the total amount of HFO-1123 and the compound(s). Further, the total proportion of the compound(s) other than HFO-1123 contained in the composition is preferably less than 0.5 mass % based on the total amount of HFO-1123 and the compound(s). Further, the lower limit of the total proportion of the compound(s) is preferably 0.0001 mass %.

As described above, by hydrogen reduction of CTFE, a composition containing HFO-1123 of the present invention can be obtained.

(II) Synthesis Involving Heat Decomposition of R22 and R31

HFO-1123 is produced by a synthetic reaction involving heat decomposition using a material composition containing R22 and R31 in the presence of a heating medium.

This production process comprises:

(a) a step of supplying R22 and R31 in a molar ratio of 1:0.01 to 4.0 as preliminarily mixed or separately to a reactor and allowing them to stay in the reactor for a predetermined time, and (b) a step of supplying a heating medium to the reactor and bringing the heating medium into contact with the material composition supplied to the reactor and staying for a predetermined time in the step (a).

According to this embodiment, HFO-1123 which has a low GWP and which is useful as a new refrigerant can be efficiently produced by a single reaction using R22 and R31 as the material. Further, according to this embodiment, it is easy to control the production (reaction) conditions particularly to control the temperature conditions since the heating medium is used, and it is thereby possible to produce HFO-1123 more quantitatively. Further, it is possible to reuse by-products which may form $F_2C$: as material components, and such is economically advantageous.

This process may be a continuous production process or may be a batch production process. In a continuous production process, supply of the material composition containing R22 and R31 in the above proportion to the reactor and supply of the heating medium to the container are continuously carried out, and the steps (a) and (b) are carried out simultaneously. In a batch production process, either of supply of the material composition in the step (a) and supply of the heating medium in the step (b) may be carried out first, or both may be carried out simultaneously. That is, even when one of the material composition and the heating medium is not supplied to the reactor at the time of supply of the other one, while the material composition or the heating medium which has been supplied first stays in the reactor, the other component is supplied, and the material composition and the heating medium are contacted with each other in the reactor for a predetermined time.

This production process is preferably a continuous process in view of the production efficiency. Now, production of HFO-1123 by a continuous production process will be described.

The main reaction in the reactor in this embodiment is shown in the following formula (2):

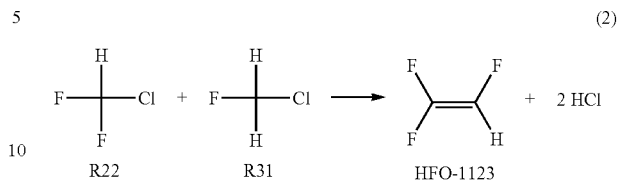

It is considered that the material composition containing R22 and R31 is subjected to heat decomposition and a dehydrochlorination reaction in the reactor to form a reaction mixture containing difluorocarbene ($F_2C$:) and R31, and the reaction mixture is converted to HFO-1123 by addition reaction directly or by means of two or more intermediates.

<Material Composition>

The material composition to be used for production of HFO-1123 by the above reaction contains R22 and R31.

With respect to the ratio of R22 and R31 in the material composition, the proportion of R31 is within a range of from 0.01 to 4.0 mole per 1 mole of R22. That is, the molar ratio of the amount of R31 supplied to the amount of R22 supplied to the reactor (R31/R22, where R31 is the molar amount of R31 supplied and R22 is the molar amount of R22 supplied) is from 0.01 to 4.0. In this embodiment in which the material composition and the heating medium are made to continuously flow through the reactor to carry out the reaction, the amounts of the material components and the heating medium supplied are amounts of supply per unit time.

When the R31/R22 ratio is within the above range, the inversion rate (reaction rate) of the material components particularly the inversion rate of R31 can be made high. Further, the proportion of components other than HFO-1123, i.e. by-products in the obtained reaction product can be suppressed. The R31/R22 ratio is more preferably within a range of from 0.1 to 4.0, particularly preferably from 0.1 to 1.5.

The material composition may contain, in addition to such two components, a fluorinated compound which may undergo heat decomposition in the reactor to form $F_2C$:, such as TFE (FO-1114), FO-1216, RC318, VdF (HFO-1132a), HFO-1113 or HFO-1123. When such a fluorinated compound which may undergo heat decomposition in the reactor to form $F_2C$: is used for the material composition, although a separately prepared fluorinated compound may be used, a fluorinated compound which is formed as a by-product by the heat decomposition reaction of R22 and R31 according to this embodiment is preferably used from the viewpoint of recycle.

The material composition containing R22 and R31 may be introduced to the reactor as it is at room temperature, or its temperature when it is introduced to the reactor may be adjusted e.g. by heating, so as to improve the reactivity in the reactor. However, the temperature ranges suitable to improve the reactivity of the fluorinated compound which may form $F_2C$: including R22 and of R31 are different from each other, and thus their temperature adjustments are preferably carried out separately.

The temperature of R31 to be supplied to the reactor and the temperature of the fluorinated compound which may form $F_2C$: including R22 to be supplied to the reactor, are preferably from 0 to 600° C., so that the reactivity is high to a certain extent but carbonization is less likely to occur.

With a view to further increasing the reactivity, R22 or the fluorinated compound which may form $F_2C$: including R22 is preferably heated to the room temperature (25° C.) or higher and 600° C. or lower before introduction into the reactor, more preferably heated to 100 to 500° C.

Further, the temperature of R31 to be supplied to the reactor is preferably from 0 to 1,200° C. from the viewpoint of the reactivity. With a view to further increasing the reactivity, R31 is preferably heated to room temperature or higher and 1,200° C. or lower before introduction to the reactor, more preferably heated to 100 to 800° C.

R22 and R31 and further, the fluorinated compound which may form $F_2C$: to be used as the case requires, may be separately supplied to the reactor, or they may be mixed and then supplied. In a case where the respective components are mixed and then supplied, the respective components may be divided into groups, for example, they are divided into the fluorinated compound which may form $F_2C$: and the other components, the respective components are mixed in each group and the mixtures of the respective groups are separately supplied to the reactor, or all the components are mixed and then supplied. Considering the above difference in the temperature conditions, it is preferred to mix the fluorinated compounds which may form $F_2C$: including R22, adjust the mixture to the above preferred temperature and supply such a mixture, and separately, to adjust R31 to the above preferred temperature and supply it to the reactor.

<Heating Medium>

The heating medium in this embodiment is supplied to the reactor so that it is contacted with the material composition in the reactor for a predetermined time. The heating medium is a medium which does not undergo heat decomposition at the temperature in the reactor, and is specifically preferably a medium which does not undergo heat decomposition at a temperature of from 100 to 1,200° C. The heating medium may be a gas of one or more selected from water vapor, nitrogen and carbon dioxide. Preferred is use of a gas containing water vapor in an amount of at least 50 vol % and containing nitrogen and/or carbon dioxide as the rest. In order to remove HCl formed by the reaction of the above formula (2) as hydrochloric acid, the content of water vapor in the heating medium is preferably at least 50 vol %, and particularly preferred is use of a gas consisting substantially of water vapor alone (100 vol %).

The amount of the heating medium supplied is preferably such that the proportion of the heating medium is from 20 to 98 vol %, more preferably from 50 to 95 vol % based on the total amount of the heating medium and the material composition supplied. When the proportion of the heating medium supplied is at least 20 vol % based on the total amount of the heating medium and the material composition supplied, heat decomposition and synthesis reaction of the above formula (2) proceed while formation of high-boiling point substances and carbonization of the material components are suppressed, whereby HFO-1123 can efficiently be produced. Further, the above proportion exceeding 98 vol % is not industrially realistic since the productivity will remarkably decrease.

The time of contact of the heating medium and the material composition supplied in the reactor is preferably from 0.01 to 10 seconds, more preferably from 0.2 to 3.0 seconds. When the contact time is from 0.01 to 10 seconds, the reaction to form HFO-1123 will sufficiently proceed, and formation of by-products can be suppressed. The time of contact of the heating medium and the material composition corresponds to the retention time of the material composition in the reactor, and can be controlled by adjusting the amount of supply (flow rate) of the material composition into the reactor.

<Reactor>

The shape of the reactor is not particularly limited so long as the reactor can withstand the after-mentioned temperature and pressure in the reactor, and for example, a cylindrical vertical reactor may be mentioned. A material of the reactor may, for example, be glass, iron, nickel, or an alloy containing iron or nickel as the main component.

The temperature in the reactor in the step (b) is preferably from 400 to 1,200° C., more preferably from 600 to 900° C., particularly preferably from 710 to 900° C. When the temperature in the reactor is within a range of from 400 to 1,200° C., the reactivity of the synthetic reaction involving heat decomposition represented by the above formula (2) can be increased, and HFO-1123 can be obtained efficiently.

The temperature in the reactor may be controlled by adjusting the temperature and the pressure of the heating medium supplied to the reactor. Further, the interior of the reactor may be supplementarily heated e.g. by an electric heater so that the temperature in the reactor is within the particularly preferred temperature range (710 to 900° C.).

The pressure in the reactor is preferably from 0 to 2.0 MPa, more preferably from 0 to 0.5 MPa by the gauge pressure.

<Outlet Gas Component>

By such synthesis involving heat decomposition of R22 and R31, a composition containing HFO-1123 can be obtained as an outlet gas of the reactor. Compounds other than HFO-1123 contained in the outlet gas may, for example, be R22 and R31 as the unreacted materials, and HFO-1132, HFO-1132a, HFO-1141, CFO-1113, HCFO-1122, HCFO-1122a, HFC-143, FO-1114, HCFO-1131, HFO-1252zf, HFO-1243zf, HFO-1234yf, HFO-1234ze, FO-1216, HFC-125, HFC-134, HFC-134a, HFC-143a, HCFC-124, HCFC-124a, HFC-227ca, HFC-227ea, HFC-236fa, HFC-236ea, CFC-12, HFC-23, HFC-32, HFC-41, chloromethane, RC-318 and methane.

The above components other than HFO-1123 contained in the outlet gas may be removed to the desired level by a known means such as distillation. Particularly purification by distillation is preferred. And, separated FO-1114 (TFE), FO-1216 (HFP), CFO-1113 (CTFE) and RC318 are compounds which may form $F_2C$:, and may be recycled as a part of the material composition.

The composition containing HFO-1123 obtained by purification is preferably a composition containing, in addition to HFO-1123, at least one compound selected from the group consisting of E-1,2-difluoroethylene, Z-1,2-difluoroethylene, 1,1-difluoroethylene, chlorotrifluoroethylene, tetrafluoroethylene, fluoroethylene, 1,1,1-trifluoroethane, difluoromethane, trifluoromethane and pentafluoroethane.

The proportion of each of the above compound(s) other than HFO-1123 contained is preferably less than 0.5 mass % based on the total amount of HFO-1123 and the compound(s). Further, the total proportion of the above compound(s) other than HFO-1123 contained in the composition is preferably less than 0.5 mass % based on the total amount of HFO-1123 and such compound(s). Further, the lower limit of the total proportion of such compound(s) is preferably 0.0001 mass %.

As described above, by synthesis involving heat decomposition of R22 and R31, the composition containing HFO-1123 of the present invention can be obtained.

EXAMPLES

Now, the present invention will be described in further detail with reference to Examples. However, it should be understood that the present invention is by no means restricted to such specific Examples.

Example 1

A reaction tube made of stainless steel having an inner diameter of 2.3 cm and a length of 50 cm, was filled with palladium-supporting activated carbon having 0.5 part by mass of palladium supported on 100 parts by mass of coconut shell activated carbon to form a catalyst layer having a height of 40 cm. The density of the palladium-supporting activated carbon in the catalyst layer was 0.74 g/cm$^3$.

The catalyst layer thus formed in the reaction tube was controlled to be 80° C. by an electric heater, and a material composition containing CTFE and hydrogen (hereinafter sometimes referred to as a material gas) was supplied to the reaction tube under an internal pressure (gauge pressure) of 0.04 MPa. Hereinafter the pressure means a gauge pressure.

The material gas was made to flow through the reaction tube so that the molar ratio (hydrogen/CTFE) of hydrogen to CTFE in the material gas would be 1.0. The time of contact of the material gas to the catalyst layer was 30 seconds, and the linear velocity u of the material gas component (CTFE) was 1.3 cm/sec.

The maximum temperature of the catalyst layer during the reaction was measured by a bulk thermometer inserted into the catalyst layer while its position was moved. The maximum temperature of the catalyst layer was 236° C.

An outlet gas collected at an outlet of the reactor contains the unreacted material gas in addition to gases formed by the reaction and gases formed as by-products, and hereinafter the outlet gas may sometimes be referred to as a formed gas.

Then, the formed gas discharged from the outlet of the reaction tube was washed with an alkali and then dehydrated, and then analyzed by gas chromatography to calculate the molar composition of gas components contained in the outlet gas. Further, based on the molar composition of the outlet gas, the inversion rate (reaction rate) of CTFE was obtained. The results are shown in Table 3 together with the production conditions.

Further, as mentioned above, the inversion rate of CTFE means the proportion (mol %) of the reacted CTFE, and when the proportion (yield) of CTFE in the outlet gas is X %, the inversion rate of CTFE is (100−X) %.

TABLE 3

| Production conditions | | |
|---|---|---|
| Maximum temperature in reactor | | 236° C. |
| Internal pressure in reactor (gauge pressure) | | 0.04 MPa |
| Retention time [sec.] | | 30 |
| Hydrogen/CTFE supply ratio | | 1.0 |
| CTFE inversion rate | | 91.0 |

| Crude HFO-1123 | | | |
|---|---|---|---|
| | Boiling point | Composition | |
| Compound names | [° C.] | mol % | mass % |
| Methane | −161.6 | 0.02 | 0.003 |
| VdF | −83 | 0.97 | 0.70 |
| HFO-1123 | −55 | 70.57 | 65.57 |
| (E)-HFO-1132 | −53.1 | 0.04 | 0.03 |
| CTFE | −28.4 | 9.02 | 11.86 |
| (Z)-HCFO-1132 | −26 | 0.22 | 0.16 |
| HFC-152a | −24 | 0.01 | 0.007 |
| HCFO-1122 | −18 | 0.05 | 0.06 |
| HCFO-1122a | −15 | 0.15 | 0.17 |
| HCFC-142b | −9 | 0.08 | 0.09 |
| HCFO-1122a | −5 | 0.16 | 0.18 |
| HFC-143 | 5 | 12.82 | 12.20 |
| HCFC-133b | 12 | 1.65 | 2.21 |
| CFO-1112 | 15 | 0.03 | 0.04 |
| HCFC-133 | 17 | 0.56 | 0.75 |
| HCFC-142 | 24 | 0.02 | 0.02 |
| HCFC-123a | 28 | 3.36 | 5.79 |
| CFC-113 | 47.6 | 0.08 | 0.17 |
| Total | | 100 | 100 |

Then, the crude HFO-1123 composition obtained by the above production process is recovered, and supplied to a 21st plate from the top of a distillation column with 30 plates in a rate of 8,836.8 g/h, and distillation is carried out continuously under an operation pressure of 1.0 MPa (gauge pressure) at a column top temperature of 4.9° C. at a column bottom temperature of 36.9° C. On that occasion, the reflux is supplied to the uppermost plate of the distillation column.

Further, by operation at a reflux ratio of 21.0, a fraction having low-boiling point components concentrated is distilled at a rate of 916.8 g/h (distillate 1), HFO-1123 with high purity is distilled from a portion at a temperature in the column of 9.0° C., i.e. a 14th plate from the top, at a rate of 3,705.1 g/h (distillate 2) and further distilled from the bottom at a rate of 4,214.9 g/h (bottom liquid). The compositions of the distillates and the bottom liquid, the column top temperature, the temperature at the 14th plate and the bottom temperature are shown in Table 4.

TABLE 4

| Compound names | Boiling point [° C.] | Amount of crude HFO-1123 supplied to distillation column | | | Distillate 1 | | Distillate 2 (HFO-1123 product) | | | Bottom liquid | |
|---|---|---|---|---|---|---|---|---|---|---|---|
| | | [mol %] | [mass %] | [g/h] | [g/h] | [mass %] | [g/h] | [mass %] | [mass ppm] | [g/h] | [mass %] |
| Methane | −161.6 | 0.02 | 0.003 | 0.321 | 0.315 | 0.034 | 0.006 | 0.0002 | 1.6 | 0.000 | 0.000 |
| VdF | −83 | 0.97 | 0.703 | 60.833 | 52.289 | 5.703 | 8.537 | 0.2304 | 2304.0 | 0.008 | 0.000 |
| HFO-1123 | −55 | 70.57 | 65.569 | 5786.740 | 864.081 | 94.245 | 3690.043 | 99.5937 | | 1232.617 | 29.245 |
| (E)-HFO-1132 | −53.1 | 0.04 | 0.029 | 2.560 | 0.164 | 0.018 | 1.466 | 0.0396 | 395.6 | 0.931 | 0.022 |
| CTFE | −28.4 | 9.02 | 11.856 | 1050.559 | 0.000 | 0.000 | 4.949 | 0.1336 | 1335.7 | 1045.610 | 24.808 |
| (Z)-HFO-1132 | −26 | 0.22 | 0.160 | 14.080 | 0.000 | 0.000 | 0.053 | 0.0014 | 14.2 | 14.028 | 0.333 |
| HFC-152a | −24 | 0.01 | 0.007 | 1.321 | 0.000 | 0.000 | 0.005 | 0.0001 | 1.2 | 1.316 | 0.031 |
| HCFO-1122 | −18 | 0.05 | 0.056 | 4.924 | 0.000 | 0.000 | 0.004 | 0.0001 | 1.1 | 4.920 | 0.117 |
| HCFO-1122a | −15 | 0.15 | 0.167 | 19.700 | 0.000 | 0.000 | 0.017 | 0.0005 | 4.6 | 19.683 | 0.467 |
| HCFC-142b | −9 | 0.08 | 0.091 | 6.030 | 0.000 | 0.000 | 0.001 | 0.0000 | 0.2 | 6.029 | 0.143 |
| HCFO-1122a | −5 | 0.16 | 0.178 | 16.745 | 0.000 | 0.000 | 0.001 | 0.0000 | 0.2 | 16.744 | 0.397 |
| HFC-143 | 5 | 12.82 | 12.202 | 1077.406 | 0.000 | 0.000 | 0.017 | 0.0005 | 4.6 | 1077.388 | 25.562 |
| HCFC-133b | 12 | 1.65 | 2.206 | 194.700 | 0.000 | 0.000 | 0.000 | 0.0000 | | 194.700 | 4.619 |

TABLE 4-continued

| Compound names | Boiling point [° C.] | Amount of crude HFO-1123 supplied to distillation column | | | Distillate 1 | | Distillate 2 (HFO-1123 product) | | | Bottom liquid | |
|---|---|---|---|---|---|---|---|---|---|---|---|
| | | [mol %] | [mass %] | [g/h] | [g/h] | [mass %] | [g/h] | [mass %] | [mass ppm] | [g/h] | [mass %] |
| CFO-1112 | 15 | 0.03 | 0.045 | 3.960 | 0.000 | 0.000 | 0.000 | 0.0000 | | 3.960 | 0.094 |
| HCFC-133 | 17 | 0.56 | 0.749 | 66.080 | 0.000 | 0.000 | 0.000 | 0.0000 | | 66.080 | 1.568 |
| HCFC-142 | 24 | 0.02 | 0.023 | 2.010 | 0.000 | 0.000 | 0.000 | 0.0000 | | 2.010 | 0.048 |
| HCFC-123a | 28 | 3.36 | 5.787 | 513.850 | 0.000 | 0.000 | 0.000 | 0.0000 | | 513.850 | 12.191 |
| CFC-113 | 47.6 | 0.08 | 0.170 | 14.990 | 0.000 | 0.000 | 0.000 | 0.0000 | | 14.990 | 0.356 |
| Total | | 100 | 100 | 8836.8 | 916.8 | 100 | 3705.1 | 100 | | 4214.9 | 100 |
| Column top temperature [° C.] | | | | | 4.900 | | | | | | |
| Temperature at 14th plate [° C.] | | | | | | | 9.000 | | | | |
| Column bottom temperature [° C.] | | | | | | | | | | 36.9 | |

It is found from the above Example that HFO-1123 (distillate 2 in Table 4) obtained by the present production process contains methane, VdF, (E)-HFO-1132, CTFE, (Z)-HFO-1132, HFC-152a, HCFO-1122a, HCFO-1122, HCFC-142b and HFC-143 in a total content of less than 0.5 wt %.

Example 2

Crude HFO-1123 was obtained from a material gas containing R22 and R31 as follows.

Into a tube made of stainless steel in an electric furnace the temperature in which was set at 300° C., a material gas containing R31 and R22 in a molar ratio (R31/R22) of 1.0 was continuously introduced, followed by heating to 300° C.

Then, the material gas (R31 and R22) which was preliminarily heated and adjusted to the above temperature as mentioned above, and water vapor heated by an electric furnace the temperature in which was set at 750° C., were supplied to a reactor controlled to have an internal pressure (gauge pressure) of 0.04 MPa and an internal temperature of 750° C. so that the proportion of water vapor supplied based on the entire amount of the gases supplied was such that water vapor/(R31+R22+water vapor)×100=90% by vol %.

The flow rate (amount of supply per unit time) of the material gas was controlled so that the retention time of the material gas in the reactor would be 0.5 second, and a formed gas was collected at an outlet of the reactor. The measured value of the temperature in the reactor was 750° C., and the measured value of the pressure in the reactor was 0.042 MPa.

Then, the formed gas collected at the outlet of the reactor was cooled to 100° C. or lower, recovery of vapor and an acidic liquid and washing with an alkali were sequentially carried out, and then the gas was dehydrated and analyzed by gas chromatography to calculate the molar composition of gas components contained in the outlet gas. The production conditions are shown in Table 5, and the composition of the obtained crude HFO-1123 is shown in Table 6.

Here, the temperature of the material gas (R31 and R22) was the set temperature in the above electric furnace for preheating, and the water vapor temperature is the set temperature in the electric furnace for water vapor heating.

TABLE 5

| | | |
|---|---|---|
| Production conditions | Temperature in reactor (° C.) | 750 |
| | Pressure (gauge pressure) in reactor (MPa) | 0.04 |
| | Retention time (s) | 0.5 |

TABLE 5-continued

| | |
|---|---|
| R31/R22 ratio (molar ratio) | 1.0 |
| Material gas temperature (° C.) | 300 |
| (Water vapor)/(R31 + R22 + water vapor) × 100 (vol %) | 90 |
| Water vapor temperature (° C.) | 750 |

TABLE 6

| Compound names | Boiling point [° C.] | Crude HFO-1123 mol % | Crude HFO-1123 mass % |
|---|---|---|---|
| Methane | −161.6 | 6.43 | 1.36 |
| VdF | −83 | 4.98 | 4.19 |
| HFC-23 | −82.1 | 13.48 | 12.41 |
| HFC-41 | −78.2 | 3.84 | 1.72 |
| TFE | −76.3 | 15.08 | 19.82 |
| HFO-1141 | −72.2 | 0.06 | 0.04 |
| HFO-1123 | −55 | 12.32 | 13.28 |
| (E)-HFO-1132 | −53.1 | 0.27 | 0.23 |
| HFC-32 | −51.6 | 0.02 | 0.01 |
| HFC-125 | −48.5 | 0.71 | 1.12 |
| HFC-143a | −47 | 0.42 | 0.47 |
| HCFC-22 | −40.7 | 6.41 | 7.29 |
| HFO-1252zf | −30 | 0.01 | 0.01 |
| CFC-12 | −29.8 | 0.01 | 0.02 |
| HFO-1234yf | −29 | 0.65 | 0.97 |
| HFP | −29 | 0.22 | 0.44 |
| CTFE | −28.4 | 1.61 | 2.46 |
| (Z)-HFO-1132 | −26 | 0.95 | 0.80 |
| HFC-134a | −26 | 4.80 | 6.43 |
| HCC-40 | −24.2 | 1.49 | 0.99 |
| HFC-134 | −23 | 1.38 | 1.86 |
| HFO-1243zf | −22 | 0.03 | 0.04 |
| HFO-1234ze | −19 | 0.10 | 0.15 |
| HCFO-1122 | −19 | 0.20 | 0.26 |
| HFC-227ea | −18 | 0.29 | 0.65 |
| HFC-227ca | −16 | 0.23 | 0.52 |
| HCFO-1122a | −15 | 0.08 | 0.10 |
| HCFC-124 | −12 | 0.08 | 0.14 |
| HCFC-31 | −9.1 | 22.72 | 20.44 |
| HCFC-124a | −9 | 0.09 | 0.16 |
| RC-318 | −6 | 0.11 | 0.29 |
| HFC-236fa | −1.1 | 0.11 | 0.22 |
| HFC-143 | 5 | 0.53 | 0.58 |
| HFC-236ea | 10 | 0.26 | 0.52 |
| Total | | 100.00 | 100.00 |

The above crude HFO-1123 is supplied to a 15th plate from the top of a distillation column (distillation column 1) with 30 plates at a rate of 7,533 g/h, and distillation is carried out continuously under an operation pressure of 1.5 MPa (gauge pressure) at a column top temperature of −54° C. at a column bottom temperature of 40.3° C. On that occasion, the reflux is supplied to the uppermost plate of the distillation column.

Then, by operation with a reflux ratio of 10.0, a fraction having low-boiling point components concentrated is distilled from the top of the distillation column 1 at a rate of 2,987 g/h (distillate 1), and further a component containing HFO-1123 is distilled from the bottom at a rate of 4,546 g/h (bottom liquid 1).

Then, the bottom liquid recovered from the bottom of the distillation column 1 is supplied to a 48th plate from the top of a distillation column (distillation column 2) with 50 plates at a rate of 4,546 g/h, and distillation is carried out continuously under an operation pressure of 1.0 MPa (gauge pressure) at a column top temperature of 9.2° C. at a column bottom temperature of 45.7° C. On that occasion, the reflux is supplied to the uppermost plate of the distillation column.

Further, by operation with a reflux ratio of 50.0, highly purified HFO-1123 is distilled from the top of the distillation column 2 at a rate of 186 g/h (distillate 2), a fraction is distilled from a 46th plate from the top at a rate of 854.4 g/h (distillate 3), and a bottom liquid (bottom liquid 2) is recovered from the bottom at a rate of 3,505.4 g/h.

The compositions of the distillates and the bottom liquids, the column top temperature, the temperature at the 46th plate, and the column bottom temperature are shown in Tables 7 and 8.

TABLE 7

| | | Distillation column 1 | | | | | |
|---|---|---|---|---|---|---|---|
| Compound names | Boiling point [° C.] | Amount of crude HFO-1123 supplied | | Distillate 1 | | Amount of bottom liquid 1 supplied to distillation column 2 | |
| | | mol % | [g/h] | [mass %] | [g/h] | [mass %] | [g/h] | [mass %] |
| Methane | −161.6 | 6.43 | 102.194 | 1.357 | 102.194 | 3.421 | 0.000 | 0.000 |
| VdF | −83 | 4.98 | 315.693 | 4.191 | 315.689 | 10.569 | 0.004 | 0.000 |
| HFC-23 | −82.1 | 13.48 | 934.687 | 12.408 | 934.685 | 31.292 | 0.002 | 0.000 |
| HFC-41 | −78.2 | 3.84 | 129.325 | 1.717 | 129.322 | 4.329 | 0.004 | 0.000 |
| TFE | −76.3 | 15.08 | 1493.239 | 19.823 | 1493.046 | 49.984 | 0.193 | 0.004 |
| HFO-1141 | −72.2 | 0.06 | 2.763 | 0.037 | 2.754 | 0.092 | 0.009 | 0.000 |
| HFO-1123 | −55 | 12.32 | 1000.400 | 13.280 | 9.222 | 0.309 | 991.178 | 21.804 |
| (E)-HFO-1132 | −53.1 | 0.27 | 17.280 | 0.229 | 0.036 | 0.001 | 17.244 | 0.379 |
| HFC-32 | −51.6 | 0.02 | 1.041 | 0.014 | 0.037 | 0.001 | 1.003 | 0.002 |
| HFC-125 | −48.5 | 0.71 | 84.015 | 1.115 | 0.026 | 0.001 | 83.990 | 1.848 |
| HFC-143a | −47 | 0.42 | 35.297 | 0.469 | 0.003 | 0.000 | 35.294 | 0.776 |
| HCFC-22 | −40.7 | 6.41 | 549.072 | 7.289 | 0.005 | 0.000 | 549.067 | 12.078 |
| HFO-1252zf | −30 | 0.01 | 0.780 | 0.010 | 0.000 | 0.000 | 0.780 | 0.017 |
| CFC-12 | −29.8 | 0.01 | 1.209 | 0.016 | 0.000 | 0.000 | 1.209 | 0.027 |
| HFO-1234yf | −29 | 0.65 | 72.960 | 0.969 | 0.000 | 0.000 | 72.960 | 1.605 |
| HFP | −29 | 0.22 | 33.005 | 0.438 | 0.000 | 0.000 | 33.005 | 0.726 |
| CTFE | −28.4 | 1.61 | 185.187 | 2.458 | 0.000 | 0.000 | 185.187 | 4.074 |
| (Z)-HFO-1132 | −26 | 0.95 | 60.160 | 0.799 | 0.000 | 0.000 | 60.160 | 1.323 |
| HFC-134a | −26 | 4.80 | 484.643 | 6.434 | 0.000 | 0.000 | 484.643 | 10.661 |
| HCC-40 | −24.2 | 1.49 | 74.722 | 0.992 | 0.000 | 0.000 | 74.722 | 1.644 |
| HFC-134 | −23 | 1.38 | 139.783 | 1.856 | 0.000 | 0.000 | 139.783 | 3.075 |
| HFO-1243zf | −22 | 0.03 | 2.882 | 0.038 | 0.000 | 0.000 | 2.882 | 0.063 |
| HFO-1234ze | −19 | 0.10 | 11.400 | 0.151 | 0.000 | 0.000 | 11.400 | 0.251 |
| HCFO-1122 | −19 | 0.20 | 19.696 | 0.262 | 0.000 | 0.000 | 19.696 | 0.433 |
| HFC-227ea | −18 | 0.29 | 49.309 | 0.654 | 0.000 | 0.000 | 49.309 | 1.085 |
| HFC-227ca | −16 | 0.23 | 39.107 | 0.519 | 0.000 | 0.000 | 39.107 | 0.860 |
| HCFO-1122a | −15 | 0.08 | 7.880 | 0.105 | 0.000 | 0.000 | 7.880 | 0.173 |
| HCFC-124 | −12 | 0.08 | 10.918 | 0.145 | 0.000 | 0.000 | 10.918 | 0.240 |
| HCFC-31 | −9.1 | 22.72 | 1540.070 | 20.444 | 0.000 | 0.000 | 1540.070 | 33.878 |
| HCFC-124a | −9 | 0.09 | 12.283 | 0.163 | 0.000 | 0.000 | 12.283 | 0.270 |
| RC-318 | −6 | 0.11 | 22.003 | 0.292 | 0.000 | 0.000 | 22.003 | 0.484 |
| HFC-236fa | −1.1 | 0.11 | 16.724 | 0.222 | 0.000 | 0.000 | 16.724 | 0.368 |
| HFC-143 | 5 | 0.53 | 43.701 | 0.580 | 0.000 | 0.000 | 43.701 | 0.961 |
| HFC-236ea | 10 | 0.26 | 39.530 | 0.524 | 0.000 | 0.000 | 39.530 | 0.870 |
| Total | | 100 | 7533.0 | 100 | 2987.0 | 100 | 4545.9 | 100 |
| Operation pressure [MPa (gauge pressure)] | | | | | 1.5 | | | |
| Column top temperature [° C.] | | | | | −54.0 | | | |
| Column bottom temperature [° C.] | | | | | | | 36.9 | |
| Temperature at 46th plate [° C.] | | | | | | | | |

TABLE 8

| Compound names | Boiling point [° C.] | Distillation column 2 | | | | | |
|---|---|---|---|---|---|---|---|
| | | Distillate 2 (HFO-1123) | | | Distillate 3 | | Bottom liquid 2 | |
| | | [g/h] | [mass %] | [mass ppm] | [g/h] | [mass %] | [g/h] | [mass %] |
| Methane | −161.6 | 0.000 | 0.0000 | | 0.000 | 0.000 | 0.000 | 0.000 |
| VdF | −83 | 0.003 | 0.0017 | 17 | 0.000 | 0.000 | 0.000 | 0.000 |
| HFC-23 | −82.1 | 0.002 | 0.0010 | 10 | 0.000 | 0.000 | 0.000 | 0.000 |
| HFC-41 | −78.2 | 0.004 | 0.0019 | 19 | 0.000 | 0.000 | 0.000 | 0.000 |
| TFE | −76.3 | 0.168 | 0.0900 | 900 | 0.014 | 0.002 | 0.006 | 0.000 |
| HFO-1141 | −72.2 | 0.007 | 0.0040 | 40 | 0.001 | 0.000 | 0.001 | 0.000 |
| HFO-1123 | −55 | 185.277 | 99.5101 | | 453.581 | 53.083 | 352.314 | 10.051 |
| (E)-HFO-1132 | −53.1 | 0.281 | 0.1509 | 1509 | 8.634 | 1.010 | 8.329 | 0.238 |
| HFC-32 | −51.6 | 0.369 | 0.1980 | 1980 | 0.338 | 0.040 | 0.296 | 0.008 |
| HFC-125 | −48.5 | 0.078 | 0.0419 | 419 | 45.022 | 5.269 | 38.889 | 1.109 |
| HFC-143a | −47 | 0.001 | 0.0005 | 5 | 15.994 | 1.872 | 19.299 | 0.551 |
| HCFC-22 | −40.7 | 0.000 | 0.0000 | | 153.384 | 17.951 | 395.682 | 11.288 |
| HFO-1252zf | −30 | 0.000 | 0.0000 | | 0.098 | 0.011 | 0.682 | 0.019 |
| CFC-12 | −29.8 | 0.000 | 0.0000 | | 0.134 | 0.016 | 1.076 | 0.031 |
| HFO-1234yf | −29 | 0.000 | 0.0000 | | 9.101 | 1.065 | 63.859 | 1.822 |
| HFP | −29 | 0.000 | 0.0000 | | 5.738 | 0.672 | 27.267 | 0.778 |
| CTFE | −28.4 | 0.000 | 0.0000 | | 20.616 | 2.413 | 164.572 | 4.695 |
| (Z)-HFO-1132 | −26 | 0.000 | 0.0000 | | 5.390 | 0.631 | 54.771 | 1.563 |
| HFC-134a | −26 | 0.000 | 0.0000 | | 59.163 | 6.924 | 425.480 | 12.138 |
| HCC-40 | −24.2 | 0.000 | 0.0000 | | 7.602 | 0.890 | 67.120 | 1.915 |
| HFC-134 | −23 | 0.000 | 0.0000 | | 10.742 | 1.257 | 129.041 | 3.681 |
| HFO-1243zf | −22 | 0.000 | 0.0000 | | 0.278 | 0.032 | 2.604 | 0.074 |
| HFO-1234ze | −19 | 0.000 | 0.0000 | | 0.664 | 0.078 | 10.737 | 0.306 |
| HCFO-1122 | −19 | 0.000 | 0.0000 | | 1.055 | 0.123 | 18.641 | 0.532 |
| HFC-227ea | −18 | 0.000 | 0.0000 | | 3.778 | 0.442 | 45.531 | 1.299 |
| HFC-227ca | −16 | 0.000 | 0.0000 | | 2.996 | 0.351 | 36.111 | 1.030 |
| HCFO-1122a | −15 | 0.000 | 0.0000 | | 0.436 | 0.051 | 7.444 | 0.212 |
| HCFC-124 | −12 | 0.000 | 0.0000 | | 0.402 | 0.047 | 10.516 | 0.300 |
| HCFC-31 | −9.1 | 0.000 | 0.0000 | | 46.965 | 5.496 | 1493.106 | 42.596 |
| HCFC-124a | −9 | 0.000 | 0.0000 | | 0.453 | 0.053 | 11.830 | 0.337 |
| RC-318 | −6 | 0.000 | 0.0000 | | 0.733 | 0.086 | 21.270 | 0.607 |
| HFC-236fa | −1.1 | 0.000 | 0.0000 | | 0.165 | 0.019 | 16.559 | 0.472 |
| HFC-143 | 5 | 0.000 | 0.0000 | | 0.602 | 0.070 | 43.100 | 1.230 |
| HFC-236ea | 10 | 0.000 | 0.0000 | | 0.391 | 0.046 | 39.139 | 1.117 |
| Total | | 186.2 | 100 | 4899 | 854.5 | 100 | 3505.3 | 100 |
| Operation pressure [MPa (gauge pressure)] | | | | | 1.0 | | | |
| Column top temperature [° C.] | | | 9.2 | | | | | |
| Column bottom temperature [° C.] | | | | | | | 45.7 | |
| Temperature at 46th plate [° C.] | | | | | 18.4 | | | |

It is found from the above Example that HFO-1123 (distillate 2 in Table 8) obtained by this production process contains VdF, trifluoromethane (HFC-23), difluoromethane (HFC-32), fluoromethane (HFC-41), pentafluoroethane (HFC-125), 1,1,1-trifluoroethane (HFC-143a), tetrafluoroethylene (TFE), vinyl fluoride (HFO-1141) and (E)-HFO-1132 in a total content of less than 0.5 wt %.

INDUSTRIAL APPLICABILITY

The composition containing HFO-1123 of the present invention is useful as a heat transfer composition, an aerosol spray, a foaming agent, a blowing agent, a solvent, a cleaning agent, a carrier fluid, a displacement drying agent, a buffing compound, a polymerization medium, an expanding agent for polyolefin and polyurethane, a gaseous dielectric, a fire-extinguishing agent, or a liquid or gaseous fire-extinguishing agent.

This application is a continuation of PCT Application No. PCT/JP2014/061764, filed on Apr. 25, 2014, which is based upon and claims the benefit of priority from Japanese Patent Application No. 2013-095491 filed on Apr. 30, 2013. The contents of those applications are incorporated herein by reference in their entireties.

What is claimed is:

1. A method for producing a composition comprising trifluoroethylene by gas-phase hydrogen reduction of chlorotrifluoroethylene, comprising:
    reacting chlorotrifluoroethylene and hydrogen in the presence of a palladium catalyst at 80° C. or higher; and
    distilling the obtained reaction product to obtain the composition comprising trifluoroethylene and at least one compound selected from the group consisting of E-1,2-difluoroethylene, Z-1,2-difluoroethylene, chlorotrifluoroethylene, 1-chloro-2,2-difluoroethylene and 1,1-difluoroethylene, and wherein a total proportion of the at least one compound in the obtained composition is from 0.0001 mass % to less than 0.5 mass % based on a total amount of the trifluoroethylene and the at least one compound.

2. The production method according to claim 1, wherein a total proportion of E-1,2-difluoroethylene, Z-1,2-difluoroethylene, chlorotrifluoroethylene, 1-chloro-2,2-difluoroethylene and 1,1-difluoroethylene in the obtained composition is from 0.0001 mass % to less than 0.5 mass % based on a total amount of trifluoroethylene, E-1,2-difluoroethylene, Z-1,2-difluoroethylene and 1,1-difluoroethylene.

3. A method for producing a composition comprising trifluoroethylene by a synthetic reaction, comprising:

subjecting a mixture of chlorodifluoromethane and chlorofluoromethane to heat decomposition in the presence of a heating medium, wherein the synthetic reaction is carried out at a temperature from 400 to 1,200° C., and distilling the obtained reaction product to obtain the composition comprising trifluoroethylene and at least one compound selected from the group consisting of E-1,2-difluoroethylene, Z-1,2-difluoroethylene, 1,1-difluoroethylene, chlorotrifluoroethylene, tetrafluoroethylene, fluoroethylene, 1,1,1-trifluoroethane, difluoromethane, trifluoromethane and pentafluoroethane.

4. The production method according to claim 3, wherein a total proportion of any of E-1,2-difluoroethylene, Z-1,2-difluoroethylene, 1,1-difluoroethylene, chlorotrifluoroethylene, tetrafluoroethylene, fluoroethylene, 1,1,1-trifluoroethane, difluoromethane, trifluoromethane and pentafluoroethane in the obtained composition is less than 0.5 mass % based on a total amount of the trifluoroethylene and E-1,2-difluoroethylene, 1,1-difluoroethylene, tetrafluoroethylene, fluoroethylene, 1,1,1-trifluoroethane, difluoromethane, trifluoromethane and pentafluoroethane.

5. The production method according to claim 3, wherein a total proportion of E-1,2-difluoroethylene, 1,1-difluoroethylene, tetrafluoroethylene, fluoroethylene, 1,1,1-trifluoroethane, difluoromethane, trifluoromethane and pentafluoroethane is less than 0.5 mass % based on a total amount of the trifluoroethylene and E-1,2-difluoroethylene, 1,1-difluoroethylene, tetrafluoroethylene, fluoroethylene, 1,1,1-trifluoroethane, difluoromethane, trifluoromethane and pentafluoroethane.

6. The production method according to claim 1, wherein the at least one compound in the obtained composition is selected from the group consisting of E-1,2-difluoroethylene, Z-1,2-difluoroethylene, 1,1-difluoroethylene, 1-chloro-2,2-difluoroethylene and 1,1-difluoroethylene.

7. The production method according to claim 1, wherein the palladium catalyst is a catalyst having palladium and a metal other than palladium supported on a carrier, wherein the metal other than palladium is selected from the group consisting of cobalt, rhodium, iridium, nickel, gold, and combinations thereof.

8. The production method according to claim 7, wherein a proportion of the metal other than palladium supported on the carrier is from 0.01 to 50 parts by mass per 100 parts by mass of the palladium.

9. The production method according to claim 3, wherein a molar ratio of chlorofluoromethane to chlorodifluoromethane in the reaction mixture is from 0.01 to 4.0.

10. The production method according to claim 3, wherein a total proportion of the at least one compound in the obtained composition is from 0.0001 mass % to less than 0.5 mass % based on a total amount of the trifluoroethylene and the at least one compound.

\* \* \* \* \*